United States Patent [19]

Conway et al.

[11] Patent Number: 4,675,344

[45] Date of Patent: Jun. 23, 1987

[54] METHOD FOR ADJUSTING METHANOL TO HIGHER ALCOHOL RATIOS

[75] Inventors: Mark M. Conway, Sanford; Craig B. Murchison; Rex R. Stevens, both of Midland, all of Mich.

[73] Assignee: The Dow Chemical Company, Midland, Mich.

[21] Appl. No.: 830,907

[22] Filed: Feb. 18, 1986

Related U.S. Application Data

[63] Continuation of Ser. No. 635,999, Jul. 30, 1984, abandoned.

[51] Int. Cl.[4] ............................................. C07C 27/06
[52] U.S. Cl. ..................................... 518/714; 502/219; 502/220
[58] Field of Search .......................................... 518/714

[56] References Cited

U.S. PATENT DOCUMENTS

| | | | |
|---|---|---|---|
| 2,490,488 | 12/1949 | Stewart | 518/714 |
| 3,928,000 | 12/1975 | Child et al. | 518/714 |
| 4,151,190 | 4/1979 | Murchison et al. | 518/714 |
| 4,151,191 | 4/1979 | Happel et al. | |
| 4,175,928 | 11/1979 | Britton et al. | |
| 4,177,202 | 12/1979 | Chang et al. | |
| 4,199,522 | 4/1980 | Murchison et al. | 518/714 |
| 4,389,335 | 6/1983 | Morrison et al. | |
| 4,511,674 | 4/1985 | Pederson | |

FOREIGN PATENT DOCUMENTS

| | | |
|---|---|---|
| 119609 | 9/1984 | European Pat. Off. |
| 149255 | 7/1985 | European Pat. Off. |
| 149256 | 7/1985 | European Pat. Off. |
| 2065490 | 7/1981 | United Kingdom |
| 2151616A | 7/1985 | United Kingdom |

OTHER PUBLICATIONS

"Catalytic Methanation", G. A. Mills and F. W. Steffgen, *Catalysis Reviews*, 8(2) 159–210 (1973), pp. 196–198.
"Synthesis of Alcohols by Hydrogenation of Carbon Monoxide", R. B. Anderson et al., *Industrial and Engineering Chemistry*, 44(10), pp. 2418–2424 (Oct. 1952).
"A Critical Analysis of Recent Advances in CO–$H_2$ Catalysis", Catalytica Associates, Inc., Santa Clara, CA 95051, Multiclient Study No. 1124 (Jun. 1980).

*Primary Examiner*—Howard T. Mars
*Attorney, Agent, or Firm*—Charles J. Enright

[57] ABSTRACT

A method for controlling the ratio of methanol to higher alcohols produced in a process for making mixed alcohols by contacting a hydrogen- and carbon monoxide-containing feed with a molybdenum- or tungsten-containing catalyst, said method comprising adjusting a concentration of a sulfur releasing substance in the feed.

11 Claims, No Drawings

METHOD FOR ADJUSTING METHANOL TO HIGHER ALCOHOL RATIOS

CROSS-REFERENCE TO RELATED APPLICATION

This is a continuation in part, of application Ser. No. 635,999 filed July 30, 1984, abandoned.

FIELD OF THE INVENTION

This invention relates to a method for varying the ratio of methanol to higher alcohols in Fischer-Tropsch process for making a mixture of alcohols.

BACKGROUND OF THE INVENTION

Almost as old as the Fischer-Tropsch process for making hydrocarbons is the Fischer-Tropsch process for making alcohols. The reaction is carried out by passing a mixture of carbon monoxide and hydrogen over a catalyst for the hydrogenation of the carbon monoxide. A typical review article is R. B. Anderson et al., *Industrial and Engineering Chemistry*, Vol. 44, No. 10, pp. 2418–2424. This paper lists a number of catalysts containing zinc, copper, chromium, manganese, thorium, iron, occasionally promoted with alkali or other materials for making various alcohols. The authors state that ethyl alcohol is a major constituent, the yield of methanol is usually very small and a tentative summary of factors favouring the production of alcohols is high pressure, low temperature, high space velocity, high recycle ratio and carbon monoxide-rich synthesis gas.

Molybdenum is known to be catalytic for the Fischer-Tropsch process and is taught in U.S. Pat. No. 4,151,190 and U.S. Pat. No. 4,199,522 which are incorporated herein by reference. The references describe some of the herein used catalysts but do not teach that the catalyst is useful for making commercially significant quantities of alcohols. These references note that hydrogen sulfide affects the activity of the catalyst.

British patent publication No. 2,065,491 discloses a process for making $C_2$ hydrocarbons from $H_2/CO$ using a catalyst comprising a group VB and/or VIB element in combination with an iron group metal as free metals, oxides or sulfides on a porous oxidic support. The authors note that the presence of $H_2S$ alters the activity and selectivity of their process.

U.S. Pat. No. 4,177,202 discloses a process for making hydrocarbons from $H_2/CO$ over a molybdena and optionally cobalt or vanadium catalyst. Selectivity to ethane is enhanced by presence of hydrogen sulfide in the feed.

U.S. Pat. No. 2,490,488 discloses that molybdenum sulfide methanation catalysts acquire Fischer-Tropsch activity when promoted with an alkaline compound of an alkali metal. The example of the invention shows a 30 percent selectivity to $C_3+$ hydrocarbons and oxygenates. Of this 30 percent, no more than 44 percent boils near or above 65° C., the boiling point of methanol. Accordingly, the maximum possible alcohol selectivity is no more than 13.2 percent (44 percent of 30 percent).

U.S. Pat. No. 2,539,414 describes a Fischer-Tropsch process with molybdenum carbide catalysts. It teaches that the catalyst may be used to form oxygenates and at column 3, lines 66–71 teaches that one might get alcohols or hydrocarbons by varying the conditions.

G. T. Morgan et al., *J. Soc. Chem. Ind.*, Vol. 51, Jan. 8, 1932, pp. 1T–7T describe a process for making alcohols with chromium/manganese oxide catalysts promoted with alkali.

A number of references teach production of alcohols using rhodium catalysts. Some of these contain molybdenum as an optional ingredient. U.S. Pat. No. 4,014,913 discloses a catalyst containing rhodium and thorium or uranium and iron or molybdenum or tungsten for the production of ethanol. U.S. Pat. No. 4,096,164 discloses the use of rhodium in combination with molybdenum or tungsten and Example A discloses that use of a molybdenum-on-silica catalyst yielded 4.4 percent oxygenates.

EPO application No.81-33,212 (Chemical Abstracts 96:51, 800a) discloses a similar process using rhodium in combination with one or more of a long list of metals which includes molybdenum.

All of the aforementioned references are hereby incorporated by reference.

U.S. application Ser. No. 474,674, filed Mar. 18, 1984, which is hereby incorporated by reference, discloses a process for producing alcohols from synthesis gas using molybdenum and tungsten catalysts. In this application it is noted that these catalysts are tolerant to hydrogen sulfide in the hydrogen/carbon monoxide feed.

U.S. application Ser. No. 622,029, filed June 18, 1984, which is hereby incorporated by reference is a continuation-in-part of U.S. Ser. No. 476,674. In it are disclosed the catalysts in the process of this invention.

To make a commercially significant alcohol process, one must use a catalyst and conditions which are highly efficient. To be efficient the catalyst must yield a high weight ratio of product per unit weight of catalyst in a given period of time. The catalyst must be stable and active for long periods of time between regenerations. This may be particularly difficult to accomplish when the $H_2$ ratio of the feed gas is low, such as less than 2 to 1. Ideally the catalyst will be sulfur tolerant and will have a high selectivity to a commercial product to avoid purification or removal and disposal of by-products and to avoid separation into two or more product streams.

When the mixed alcohols product is to be used as a fuel replacement or a fuel additive it may be desirable that the ratio of $C_1$ to $C_2+$ alcohols be no greater than a certain amount. As used in this Application the ratio of $C_1$ to $C_2+$ alcohols means the molar ratio of methanol to $C_2$ to $C_5$ alcohols such as ethanol, propanols, butanols and pentanols, taken as a whole. The term, alcohols, generally does not include alcohols present as esters or aldehydes. For example, the methanol portion of methyl acetate is not counted as methanol.

Excessive methanol is generally considered an unattractive additive to gasolines. Methanol may decrease drivability and may increase corrosion in the fuel system and may cause phase separation when used in excessive quantities. These problems may be alleviated by blending methanol with higher alcohols.

Accordingly one may wish to synthesize mixed alcohols with no more than a certain amount of methanol in the blend. Or in a similar fashion one may wish to minimize the ratio of $C_1$ to $C_2+$ alcohols in mixed alcohols so that methanol may be purchased and blended into the mixed alcohols to give the maximum acceptable $C_1$ to $C_2+$ alcohols ratio.

Up until now, a method of varying the ratio of $C_1$ to $C_2+$ alcohols short of changing catalysts or distilling the product stream has not been known. Since distillation adds an additional process step, it is desirable to be able to vary the $C_1$ to $C_{2+}$ alcohols ratio that is produced in the reaction to form the alcohols.

OBJECTS OF THE INVENTION

It is an object of this invention to adjust the ratio of $C_1$ to $C_{2+}$ alcohols produced in a Fischer-Tropsch type reaction. It is preferred object of this invention to decrease the $C_1$ to $C_{2+}$ alcohol ratio in mixed alcohols formed from $H_2/CO$ over a molybdenum or tungsten catalyst.

SUMMARY OF THE INVENTION

One or more of these objects and other objects of the invention may be obtained by a method of controlling the ratio of methanol to higher alcohols produced in a process for making mixed alcohols by contacting hydrogen and carbon monoxide feed with a molybdenum- or tungsten-containing catalyst, the method comprising adjusting a concentration of a sulfur releasing substance in the feed.

Generally increasing the concentration of the sulfur releasing compound in the $H_2/CO$ feed acts to lower the ratio of $C_1$ to $C_{2+}$ alcohols in the product. Conversely lowering the concentration of sulfur releasing compounds in the $H_2/CO$ feed generally acts to increase the ratio of $C_1$ to $C_{2+}$ alcohols in the product.

DETAILED DESCRIPTION OF THE INVENTION

The hydrogen and carbon monoxide required for this process can be obtained by methods known in the art. Examples are gasification of hydrocarbonaceous materials such as coal, high specific gravity oils, or natural gas; as a by-product of partial combustion cracking of hydrocarbons; by steam reforming of liquid or gaseous hydrocarbons; through the water-gas shift reaction; or some combination of these. The two components may also be generated separately and combined for the subject reaction. The molar ratio of hydrogen to carbon monoxide in the feed gas which contacts the catalyst ranges generally from about 0.25 to about 100, preferably from about 0.5 to about 5 and most preferably from about 0.7 to about 3.

Generally, the selectivity to alcohols is dependent on the pressure. In the normal operating ranges, the higher the pressure at a given temperature, the more selective the process will be to alcohols. The minimum contemplated pressure is about 500 psig (3.55 MPa). The preferred minimum is about 750 psig (5.27 MPa) with about 1,000 psig (7.00 MPa) being a more preferred minimum. While about 1,500 psig (10.45 MPa) to about 4,000 psig (27.7 MPa) is the most desirable range, higher pressures may be used and are limited primarily by cost of the high pressure vessels, compressors and energy costs needed to carry out the higher pressure reactions. About 10,000 psig (69.1 MPa) is a typical maximum with about 5,000 psig (34.6 MPa) a more preferred maximum. About 3,000 psig (20.8 MPa) is a most preferred maximum pressure for $MoS_2$ catalysts.

The selectivity to alcohols is also a function of temperature and is interrelated with the pressure function. The minimum temperature used is governed by productivity considerations and the fact that at temperatures below about 200° C. volatile catalytic metal carbonyls may form. Accordingly, the minimum temperature is generally about 200° C.

For a given catalyst, at a constant pressure, as the temperature increases, the selectivity to alcohols decreases. In other words, at lower pressures one is limited to lower maximum temperatures in order to obtain a given selectivity. For example, a preferred maximum temperature is about 400° C. A more preferred maximum is about 350° C. However, the most preferred range of operation is from about 240° C. to about 325° C.

The $H_2/CO$ gas hourly space velocity (GHSV) is a measure of the volume of hydrogen plus carbon monoxide gas at standard temperature and pressure passing a given volume of catalyst in an hour's time. This may range from about 100 to about 20,000 hour$^{-1}$ and preferably from about 2,000 to about 5,000 hour$^{-1}$. to the alcohols generally increases as the space velocity increases. However, conversion of carbon monoxide decreases as space velocity increases.

Preferably at least a portion of the unconverted hydrogen and carbon monoxide in the effluent gas from the reaction, more preferably after removal of product alcohols, water and carbon dioxide formed and even more preferably any hydrocarbons formed, may be recycled to the reaction. The amount of recycle is expressed as the recycle ratio which is the ratio of moles of gases in the recycle stream to the moles of gases in the fresh feed stream. A recycle ratio of zero is within the scope of the invention with at least some recycle preferred. A recycle ratio of at least about one is more preferred and at least about three is most preferred.

In addition, the synthesis should be carried out at as little feed conversion per pass as is compatible with economic constraints related to the separation of the alcohol product from unreacted feed and hydrocarbon gases. Accordingly one would increase the space velocity and recycle ratios to preferably obtain about 15-25 percent conversion per pass.

Under the most preferred conditions, alcohols may be obtained in about an 85 percent $CO_2$ free carbon selectivity. The $CO_2$ free carbon selectivity is defined as 100 times the moles of carbon present in a product fraction divided by the total moles of carbon in all products which are not $CO_2$ or unconverted feed. For example, if one mole of ethanol is found in the alcohol fraction, this is counted as 2 moles of carbon. Carbon dioxide and water are not counted as products in this calculation.

As described in the aforecited patent applications, the first component of the catalyst preferably consists essentially of molybdenum or tungsten and mixtures thereof in free or combined form. Molybdenum is most preferred. Most preferably, components containing chromium, manganese, group IIIB elements, including the lanthanides and actinides, groups IVB, VB, VIII, IB and IIB elements are excluded.

The molybdenum or tungsten may be generally present as the sulfide. It is not necessary for the practice of this invention that any particular stoichiometric sulfide be present, only that the molybdenum and tungsten are generally present in combination with sulfur. Some of the molybdenum or tungsten may be present in combination with other elements such as oxygen or as oxysulfides. The atomic ratio of sulfur to molybdenum or tungsten may range from about 0.1 to about 3 and preferably from about 1.8 to about 2.3.

The molybdenum or tungsten may be present in an amount based on the weight of the total catalyst of at least about two percent, preferably at least about 5 percent with an upper limit of about 98 percent and preferably about 30 percent of the total catalyst.

When unsupported molybdenum or tungsten is present, it is present in about stoichiometric quantities in relation to other elements with which it may be combined as a compound. Other materials would also have to be considered with respect to the fraction of catalyst that is the active metal, such as, agglomerating agents, binders, pelleting lubricants, promoters and possible other catalytic materials.

The catalyst is always promoted with a promoter which may consist essentially of one or more alkali elements or alkaline earth elements in free or combined form. Alkali elements include lithium, sodium, potassium, rubidium and cesium. Alkaline earth elements include beryllium, magnesium, calcium, strontium and barium. Alkali elements and in particular, cesium and potassium, are preferred. Potassium is most preferred.

The promoter may be present in free or combined form as a metal, oxide, carbonate, hydroxide, sulfide or as a salt or a combination of these. The alkaline promoter is preferably present at a level sufficient to render the supported catalyst or the bulk catalyst more basic. The promoter is generally present in an amount of at least about 0.05 weight percent as a free element in the finished catalyst. Preferably it is present in an amount of at least about 0.1 percent and most preferably at least 0.5 percent. Large amounts up to about 30 percent of the promoter may be present. Preferably the promoter is present at less than 20 percent.

The promoter may be added as an ingredient to the molybdenum or tungsten component or to the support or may be part of one of the other components such as sodium or potassium molybdate or as an integral part of the support. For example, carbon supports prepared from coconut shells often contain small amounts of alkali metal oxides or hydroxides or the support may contain a substantial amount of the promoter such as when the support is magnesia.

A third optional component of the catalyst is a support which may assume any physical form such as pellets, granules, beads, extrudates, etc. The supports may be coprecipitated with the active metal species, or the support in powder form may be treated with the active metal species and then used as is or formed into the aforementioned shapes, or the support may be formed into the aforementioned shapes and then treated with the active catalytic species.

The catalytic species may be dispersed on the support by methods known in the art. Examples include impregnation from solution followed by conversion to the active species, sulfiding of molybdenum or tungsten species, precipitation of the sulfides in the presence of the support or intimate physical mixing. One or more of these methods may be used. Preferred methods of placing the molybdenum or tungsten sulfide on a support are impregnation with aqueous ammonium tetrathiomolybdate or tetrathiotungstate followed by decomposition to the sulfide and in situ formation of the sulfide by contacting of soluble molybdenum or tungsten salts and a soluble sulfide in the presence of the support. The former is more preferred.

Placing of the molybdenum or tungsten sulfide on the support is preferably followed by treatment with $H_2$ at elevated temperatures, usually with 20–50 ppm $H_2S$ present.

The exemplary support materials include: the aluminas, basic oxides, the silicas, carbons, or suitable solid compounds of magnesium, calcium, strontium, barium, scandium, yttrium, lanthanum and the rare earths, titanium, zirconium, hafnium, vanadium, niobium, tantalum, thorium, uranium, and zinc, of which oxides are exemplary compounds. Preferably the supports are neutral or basic or may be rendered neutral or basic by addition of the alkaline promoters. The aluminas include the alpha, gamma, and eta types. The silicas include for example, silica gel, diatomaceous earth, and crystalline silicates.

The carbon supports, which are preferred supports, include activated carbons such as those prepared from coals and coal-like materials, petroleum-derived carbons and animal- and vegetable-derived carbons. Preferably the carbon support will have a surface area of 1–1500 $m^2/g$, more preferably 10–1000 $m^2/g$ and most preferably 100–500 $m^2/g$ as measured by the BET nitrogen test. Preferably, micropores (<20 Å) are minimized and at least twenty percent of the volume of the pores is comprised of pores having a diameter of from about 20 Å to about 600 Å. Examples include coconut shell charcoal, coals, petroleum cokes, carbons formed by pyrolyzing materials such as vinylidene chloride polymer beads, coal, petroleum coke, lignite, bones, wood, lignin, nut shells, petroleum residues, charcoals, etc.

Based upon the weight of the total catalyst, the support when present generally comprises at least about 20 percent of the catalyst and generally not more than about 98 percent of the catalyst. Preferably the support comprises at least about 50 weight percent and most preferably at least about 70 weight percent of the catalyst.

For several reasons the preferred form of the catalyst is the agglomerated sulfide. Certain forms of molybdenum sulfide are most preferred.

Methods for making molybdenum or tungsten sulfide catalysts are disclosed generally at pages 23–34 of *Sulfide Catalysts Their Properties and Applications*, O. Weisser and S. Landa, Pergamon Press, New York, 1973, the whole of which is incorporated herein by reference.

Agglomerated molybdenum sulfide catalysts may be made by thermal decomposition of ammonium tetrathiomolybdate or other thiomolybdates as disclosed in U.S. Pat. Nos. 4,243,553 and 4,243,554 which are hereby incorporated by reference, from purchased active molybdenum sulfides, or by calcining $MoS_3$. The preferred method of preparing the catalyst is by decomposing ammonium tetrathiomolybdate that is formed by reacting a solution of ammonium heptamolybdate with ammonium sulfide followed by spray drying and calcining to form the molybdenum sulfide. The molybdenum sulfide may also be precipitated directly on to a support, but the unsupported molybdenum sulfide is preferred. Tungsten sulfides may be similarly made. An unsupported catalyst preferably has a surface area of at least 10 $m^2/g$ and more preferably more than 20 $m^2/g$ as measured by the BET nitrogen surface area.

The alkali(ne earth) promoter may be added to the active catalytic element prior to, during or after the formation of the sulfide by physical mixing or solution impregnation. The active metal sulfide may then be combined with binders such as bentonite clay, and/or pelleting lubricants such as Sterotex ® and formed into shapes for use as a catalyst.

The finished catalyst may be used in a fixed bed, moving bed, fluid bed, ebullated bed or a graded bed wherein concentration and/or activity of the catalyst varies from inlet to outlet in similar manner to known catalysts. The catalyst may be used in powdered form or may be formed into shapes with or without a binder.

The catalysts of the invention may be employed individually or in combination with other inventive catalysts or with other previously proposed catalysts and activators for the claimed process. In combination with other conventional catalysts, these catalysts may tend to progressively modify the usual effects in accordance with their individual characteristics so that quantitatively intermediate results may be achieved. In short, the catalysts of the present invention may be combined, for example, with typical hydrogenation catalysts such as cobalt and nickel.

Under preferred conditions the catalyst is stable for long periods of time and under ideal conditions may be stable and active for as many as 6000 hours or more. Activity and selectivity are preferably substantially retained after 700 hours of operation, more preferably after 2000 hours and most preferably after 4000 hours operation.

The alcohol fraction formed using the aforementioned conditions may contain methanol, ethanol, 1-propanol, 2-propanol, 1-butanol, 2-butanol, 2-methyl1-propanol, 2-methyl-2-propanol and $C_5$–$C_8$ wherein the hydroxyl group may be attached to a carbon which is attached to one or two other carbon atoms.

The product mixture, as formed under preferred conditions, contains only small portions of other oxygenated compounds besides alcohols. These other compounds may not be deleterious to using the product, as is, in motor fuels.

In all cases, the alcohol fraction is formed in at least about 20 percent $CO_2$ free carbon selectivity. Preferably the alcohol fraction is formed in at least about 30 percent $CO_2$ free carbon selectivity, more preferably greater than about 50 percent and ideally can be greater than about 70 percent. By percent $CO_2$ free carbon selectivity it is meant the percent of carbon in a specific product with respect to the total carbon converted from carbon monoxide to some product other than carbon dioxide. For example, one mole of ethyl alcohol is 2 moles of carbon and would represent 50 carbon mole percent selectivity to ethanol if 4 moles of CO were converted to products other than $CO_2$.

Preferably the co-products formed with the alcohol fraction are primarily gaseous products. That is $C_1$–$C_4$ hydrocarbons. By hydrocarbons, it is meant that heteroatoms such as oxygen, sulfur and nitrogen are not present in the molecule. Preferably $C_5+$ hydrocarbons are coproduced at less than about 20 percent $CO_2$ free carbon selectivity, more preferably at less than 10 percent and most preferably at less than 5 percent. Lower amounts of normally liquid hydrocarbons make the normally liquid alcohols easier to separate from by-products.

Under preferred conditions, the amount of water formed is substantially less than the amount of alcohols formed. Typically there is less than about 20 weight percent and preferably less than about 10 weight percent water based on the quantity of alcohol. This water may be removed by known techniques. If the water content is about 2 weight percent or less based on alcohols, the water may advantageously be removed by absorption on molecular sieves. At higher water contents, one may use a water gas shift drying step as disclosed in British Pat. Nos. 2,076,015 and 2,076,423; and U.S. patent application Ser. No. 508,625 filed June 28, 1983. All of these references are hereby incorporated by reference. Use of a sulfur and molybdenum or tungsten tolerant catalyst such as Haldor Topsoe SSK is preferred in the water gas shift drying step.

Generally, selectivity to mixed alcohols may be increased by increasing pressure, space velocity, product gas recycle ratio and by decreasing conversion, $H_2/CO$ feed ratio and temperature.

We have found that by adjusting the quantity of sulfur releasing materials that are fed into the process along with the hydrogen/carbon monoxide feed, one can alter the composition of the mixed alcohols formed. While Applicants are not certain and do not wish to be limited in any way by this theory, it is thought that the sulfur in molybdenum or tungsten sulfide catalysts is labile under the reaction conditions. This means that the character of the catalyst changes over time as sulfur is removed from the surface of the catalyst during the course of the reaction. This surface sulfur may be replaced or even increased by addition of sulfur releasing compounds into the feed for the process.

By a sulfur releasing compound, it is meant that under the reaction conditions encountered in the process for converting $H_2/CO$ to mixed alcohols, the sulfur releasing compound is converted to yield an active sulfur-containing species. The active sulfur species is unknown, but requires molybdenum or tungsten and sulfur.

The mechanism of the sulfur/catalyst interaction is unknown and Applicants do not wish to be bound to any specific theory. However, in view of the time lag between adjustment of the sulfur level in the $H_2/CO$ feed and a change in the ratio of $C_1$ to $C_2+$ alcohols, it appears that the ratio is dependent on the equilibrium sulfur level on the catalyst surface.

Suitable sulfur releasing compounds are organic sulfur compounds, such as mercaptans and sulfides. Inorganic sulfur compounds may also be used as long as they yield sulfur or sulfide upon decomposition. Typical organic sulfur compounds include the mercaptans such as methyl, ethyl and propyl mercaptans, the sulfides such as diethylsulfide and thiophene. Typical inorganic sulfur releasing compounds are hydrogen sulfide, carbon disulfide and carbonyl sulfide. Hydrogen sulfide is preferred.

One may advantageously use a stream formed by flash fractionation of the alcohol product of the process as a sulfur releasing compound by recycling that stream back into the $H_2/CO$ feed. Most of the sulfur which is removed from the reactor under reaction conditions can be isolated from the alcohol product by a simple flash fractionation. The sulfur-containing compound is taken overhead as a vapor. An appropriate amount of this overhead vapor can then be recycled to the feed in order to adjust the level of sulfur releasing compound in the feed.

An additional method for adjusting the sulfur level in the feed to the alcohol synthesis is by adjusting sulfur removal efficiency in previous process steps. For example if the $H_2/CO$ mixture is formed from a sulfur containing material such as by partial combustion cracking of a crude oil, the sulfur compounds could be removed in a scrubber or absorber prior to utilization in the process for making alcohols. The efficiency of this removal process may be adjusted to obtain the desired level of the sulfur in the feed to the alcohols process.

If one wishes to maintain the current ratio of $C_1$ to $C_2+$ alcohols this can be advantageously done by adjusting the sulfur additon rate to the feed to about match the quantity of sulfur being removed in the crude product stream. If one desires to increase or decrease the $C_1$ to $C_{2+}$ alcohol ratio one may adjust the sulfur level in the feed by lowering and/or raising the addition rate of the sulfur releasing compound.

We have found that variation in the sulfur content of the feed to the previously described process can cause the methanol content of the product alcohols to vary from about 15 to about 85 weight percent with nominally the same catalysts in the reactor. In other words the weight ratio of $C_1$ to $C_{2+}$ alcohols can be varied from about 0.18:1 to about 5.7:1. This corresponds to a molar ratio of $C_1$ to $C_2$-$C_5$ alcohols of from about 0.3 to about 9. Typically lower sulfur levels in the feed result in higher methanol content while higher sulfur levels in the feed will result in lower methanol contents.

EXAMPLE 1

A hot solution (50° C.-60° C.) made by combining 10.0 g of ammonium heptamolybdate tetrahydrate [$(NH_4)_6Mo_7O_{24}\cdot4H_2O$], 2.1 g of anhydrous potassium carbonate [$K_2CO_3$], and 60 cm$^3$ of aqueous 22 percent ammonium sulfide [$(NH_4)_2S$], is added dropwise over 32 g of 12-20 mesh MBV activated carbon (available from Witco Chemical Co.) until the carbon is saturated. All but 11 cm$^3$ of the solution is used.

After air-drying at room temperature until the carbon no longer appears wet, the carbon is heated in flowing nitrogen at a rise of 2° C./min to 300° C. which is held for one hour. The following day this catalyst is air-dried at 150° C. for two hours and then is impregnated in the same manner as before using a solution made by combining 8.3 g of $(NH_4)_6Mo_7O_{24}\cdot4H_2O$, 1.8 g of $K_2CO_3$ and 50 cm$^3$ of aqueous 22 percent $(NH_4)_2S$. Seven cubic centimeters of solution are left over after the impregnation. The drying and heat treating steps are repeated.

A third impregnation is carried out using a solution made by combining 3.6 g of $(NH_4)_6Mo_7O_{24}\cdot4H_2O$, 0.8 g of $K_2CO_3$ and 30 cm$^3$ of aqueous 22 percent $(NH_4)_2S$. All of the solution is absorbed. The drying and heat treating steps are repeated a third time.

Forty cubic centimeters of this catalyst are loaded into a one-half inch (1.27 cm) tubular reactor. Mass flow meters are used to meter $H_2$, CO, $H_2S$ and $CO_2$ independently over the catalyst. A gas compressor is used to control the pressure in the reactor. A sand bath furnace is used to control the temperature in the reactor. The products from the reactor pass through gas/liquid separation at room temperature and 50-100 psig (0.45-0.79 MPa) followed by a second gas/liquid separation at ambient pressure at dry ice temperature. Both gaseous and liquid products are analyzed by gas phase chromatography.

The results one obtains are listed in Table I.

TABLE I

| Example | 1a | 1b | 1c | 1d | 1e | 1f |
|---|---|---|---|---|---|---|
| Temp. (°C.) | 268 | 270 | 312 | 320 | 302 | 296 |
| Pressure (psig) | 1500 | 2000 | 2000 | 2500 | 3000 | 3000 |
| (MPa) | 10.34 | 13.89 | 13.89 | 17.34 | 20.79 | 20.79 |
| $H_2$/CO (molar ratio) | 1.04 | 1.07 | 1.07 | 1.14 | 1.14 | 1.14 |
| GHSV (hr$^{-1}$) | 1980 | 3000 | 4200 | 3348 | 3348 | 2310 |
| Time at indicated $H_2S$ level (hours) | 49 | 238 | 17 | 51 | 104 | 48 |
| $H_2S$ added (ppm) | 40 | 0 | 138 | 138 | 0 | 110 |
| Time on stream (hours) | 49 | 312 | 563 | 614 | 718 | 766 |
| CO Conversion (%) | 8.0 | 12.0 | 19.0 | 21.2 | 26.3 | 17.0 |
| Wt. units CO converted per wt units of catalyst per hr | 0.150 | 0.337 | 0.810 | 0.638 | 0.794 | 0.353 |
| $CO_2$ produced[1] (%) | 34.0 | 20.4 | 31.4 | 35.9 | 24.4 | 29.6 |
| Selectivities[2] (%) | | | | | | |
| Gas Phase | | | | | | |
| $CH_4$ | 19.6 | 10.7 | 14.0 | 16.6 | 12.6 | 13.9 |
| $C_{2+}$ hydrocarbons | 3.7 | 1.7 | 9.2 | 13.9 | 4.7 | 4.6 |
| Subtotal | 23.3 | 12.4 | 23.2 | 31.5 | 16.3 | 18.5 |
| Liquid Phase | | | | | | |
| Methanol | 36.67 | 63.47 | 33.10 | 16.1 | 50.8 | 24.7 |
| Ethanol | 30.39 | 18.66 | 24.80 | 30.3 | 22.3 | 36.8 |
| Propanols | 8.94 | 3.33 | 12.60 | 14.4 | 6.6 | 13.1 |
| Butanols | 0.96 | 0.53 | 3.80 | 4.84 | 1.6 | 3.7 |
| Pentanols | 0.04 | — | 0.95 | 1.41 | 0.1 | 1.0 |
| Subtotal | 77.00 | 85.99 | 75.25 | 67.05 | 81.4 | 79.3 |
| Molar Ratio $C_1/C_2$-$C_5$ alcohols | 1.99 | 6.00 | 1.87 | 0.75 | 3.69 | 1.03 |
| Other oxygenates[3] and hydrocarbons | 0 | 1.61 | 1.55 | 1.45 | 2.3 | 2.2 |
| $H_2O$[4] (wt. %) | 2.1 | 1.6 | 5.2 | 6.9 | 3.1 | 4.6 |

Footnotes:
[1] 100 × moles of $CO_2$ formed for each mole of CO converted in the reactor.
[2] Selectivities, except for $CO_2$, are based on carbon mole selectivity on a $CO_2$ free basis.
[3] Assumed a carbon number of 4 for other oxygenates.
[4] Water is calculated as weight percent of the liquid phase.

It can be seen that as the level of sulfur in the feed is raised, the ratio of methanol to higher alcohols is lowered and as the level of sulfur is lowered, the ratio is raised. The ratio of methanol to higher alcohols is affected by, but is not proportional to, the sulfur level in the feed.

EXAMPLE 2

A solution of $(NH_4)_2MoS_4$ is prepared by mixing a solution of 180 g of $(NH_4)_4Mo_7O_{24}\cdot4H$ of water containing 100 cm$^3$ of concentrated $NH_4OH$ with 1300 cm$^3$ of 22 percent aqueous $(NH_4)_2S$. After stirring at 50° C.-60° C. for two hours, the $(NH_4)_2MoS_4$ solution is poured into a large shallow dish and allowed to evaporate to dryness overnight. The dry, dark red $(NH_4)_2MoS_4$ is calcined for one hour at 500° C. in nitrogen to give black $MoS_2$ which is combined in a mortar and pestle with bentonite clay, $K_2CO_3$ and Sterotex ® pelleting lubricant to yield a catalyst containing by weight 66 percent $MoS_2$, 10 percent $K_2CO_3$, 20 percent bentonite clay and 4 percent lubricant. The catalyst is then pelletized into 3.2 mm diameter pellets at 30,000 psi (207 KPa).

The experimental procedure for making alcohols is the same as Example 1 except that 20 cm$^3$ of catalyst is used in a ⅝ inch (1.59 cm) diameter reactor. The results are reported in Table II.

TABLE II

| Example | 2a | 2b | 2c | 2d | 2e |
|---|---|---|---|---|---|
| Temp. (°C.) | 260 | 275 | 282 | 275 | 265 |
| Pressure (psig) | 2000 | 2400 | 2300 | 2550 | 3050 |

TABLE II-continued

| Example | 2a | 2b | 2c | 2d | 2e |
|---|---|---|---|---|---|
| (MPa) | | | | | |
| $H_2/CO$ (molar ratio) | 1.12 | 1.25 | 1.20 | 1.10 | 1.18 |
| GHSV ($hr^{-1}$) | 3150 | 3075 | 3195 | 3390 | 5220 |
| Time at indicated $H_2S$ level (hours) | 25 | 52 | 95 | 49 | 70 |
| $H_2S$ added (ppm) | 25 | 165 | 160 | 60 | 0 |
| Time on stream (hours) | 102 | 339 | 383 | 431 | 600 |
| CO Conversion (%) | 10.2 | 21.0 | 21.8 | 16.2 | 11.2 |
| Wt. Units CO converted per wt. units of catalyst per hr | 0.158 | 0.302 | 0.334 | 0.276 | 0.281 |
| $CO_2$ produced[1] (%) | 27.0 | 31.6 | 32.8 | 26.4 | 24.5 |
| Selectivities[2] (%) | | | | | |
| Gas Phase | | | | | |
| $CH_4$ | 14.4 | 20.6 | 20.7 | 15.6 | 11.8 |
| $C_2+$ hydrocarbons | 0 | 3.0 | 3.7 | 1.9 | 0.6 |
| Subtotal | 14.4 | 23.6 | 24.4 | 17.5 | 12.4 |
| Liquid Phase | | | | | |
| Methanol | 48.9 | 30.7 | 27.4 | 37.0 | 50.5 |
| Ethanol | 25.2 | 30.1 | 31.1 | 27.8 | 25.0 |
| Propanols | 6.8 | 9.0 | 10.1 | 9.2 | 7.2 |
| Butanols | 1.6 | 2.8 | 3.0 | 3.3 | 2.0 |
| Pentanols | 0 | 1.5 | 0.9 | 0.6 | 0 |
| Subtotal | 82.5 | 74.1 | 72.5 | 77.9 | 84.7 |
| Molar Ratio $C_1/C_2$–$C_5$ alcohols | 3.20 | 1.61 | 1.38 | 2.07 | 3.28 |
| Other oxygenates[3] and hydrocarbons | 3.1 | 2.3 | 3.1 | 4.6 | 2.9 |
| $H_2O$[4] (wt. %) | 0.78 | 1.95 | 2.1 | 1.4 | 1.4 |

Footnotes:
[1]100 × moles of $CO_2$ formed for each mole of CO converted in the reactor.
[2]Selectivities, except for $CO_2$, are based on carbon mole selectivity on a $CO_2$ free basis.
[3]Assumed a carbon number of 4 for other oxygenates.
[4]Water is calculated as weight percent of the liquid phase.

Again it is seen that time progresses, the raising of the sulfur level in the feed decreases the ratio of methanol to $C_2$–$C_5$ alcohols in the product.

Although the invention has been described in considerable detail, it must be understood that such detail is for the purpose of illustration only and that many variations and modifications can be made by one skilled in the art without departing from the spirit and scope of the invention.

We claim:

1. A method for changing the ratio of methanol to higher alcohols produced in a process for making mixed alcohols under conditions sufficient to produce alcohols in at least about 20 percent $CO_2$ free carbon selectivity, said conditions including a pressure of at least about 500 psig and a temperature of at least about 200° C., by contacting a hydrogen and carbon monoxide feed with an alkali promoted molybdenum sulfide- or tungsten sulfide-containing catalyst, which catalyst excludes group VIII elements, said method comprising adjusting a concentration of a sulfur releasing substance in the feed.

2. The method of claim 1 wherein the molybdenum or tungsten are present primarily as agglomerated sulfides.

3. The method of claim 2 wherein the catalyst contains molybdenum.

4. The method of claim 1 wherein the sulfur releasing substance is hydrogen sulfide.

5. The method of claim 1 wherein the concentration of the sulfur releasing substance is changed by more than about twenty percent.

6. The method of claim 1 wherein the concentration of the sulfur releasing substance is adjusted to change the weight ratio of methanol to $C_2$–$C_5$ alcohols by at least ten percent.

7. The method of claim 6 wherein the weight ratio of methanol to $C_2$–$C_5$ alcohols is changed by at least twenty percent.

8. A method for decreasing the ratio of methanol to higher alcohols produced in a process for making mixed alcohols under conditions sufficient to produce alcohols in at least about 20 percent $CO_2$ free carbon selectivity, said conditions including a pressure of at least about 500 psig and a temperature of at least about 200° C., by contacting a hydrogen and carbon monoxide feed with an alkali promoted molybdenum sulfide- or tungsten sulfide-containing catalyst, which catalyst excludes group VIII elements, said method comprising increasing an addition rate of a sulfur releasing substance to the feed.

9. The method of claim 8 wherein methanol is less than forty weight percent of the $C_1$–$C_5$ alcohols fraction.

10. The method of claim 9 wherein methanol is less than thirty weight percent of the $C_1$–$C_5$ alcohols fraction.

11. A method for changing the weight ratio of methanol to $C_2$–$C_5$ alcohols produced by at least ten percent in a process for making mixed alcohols under conditions sufficient to produce alcohols in at least about 20 percent $CO_2$ free carbon selectivity, said conditions including a pressure of at least about 500 psig and a temperature of at least about 200° C., by contacting a hydrogen and carbon monoxide feed with an alkali promoted agglomerated molybdenum sulfide catalyst, which catalyst excludes group VIII elements, said method comprising adjusting a concentration of a sulfur releasing substance in the feed.

* * * * *

UNITED STATES PATENT AND TRADEMARK OFFICE
CERTIFICATE OF CORRECTION

PATENT NO. : 4,675,344

DATED : June 23, 1987

INVENTOR(S) : Mark M. Conway, Sanford; Craig B. Murchison; Rex R. Stevens, both of Midland, all of Mich.

It is certified that error appears in the above-identified patent and that said Letters Patent is hereby corrected as shown below:

Column 2, line 28, the word -- used -- should be inserted between "catalysts" and "in."

Column 2, line 36, "$H_2$" should read -- $H_2/CO$ --. Also, the words in the smaller print should printed in a larger type.

Column 3, line 7, -- a -- should be inserted between "is" and "preferred."

Column 4, line 13, -- Selectivity -- should be inserted before the word "to."

Column 7, line 23, insert a "-" between "2-methyl 1-." It should read "2-methyl-1-."

Column 7, line 24, insert the word -- alcohols -- between "$C_5-C_8$" and "wherein."

Column 10, line 46, the line should read, "solution of 180 g of $(NH_4)_4Mo_7O_{24} \cdot 4H_2O$ in 400 $cm^3$ of water con-."

UNITED STATES PATENT AND TRADEMARK OFFICE
CERTIFICATE OF CORRECTION

PATENT NO. : 4,675,344

DATED : June 23, 1987

INVENTOR(S) : Mark M. Conway, et al.

It is certified that error appears in the above-identified patent and that said Letters Patent is hereby corrected as shown below:

Column 11, line 40, insert the word -- as -- between "that" and "time".

Signed and Sealed this

Sixteenth Day of February, 1988

Attest:

DONALD J. QUIGG

*Attesting Officer*  *Commissioner of Patents and Trademarks*